United States Patent [19]

Liang et al.

[11] Patent Number: 5,077,192
[45] Date of Patent: Dec. 31, 1991

[54] METHOD OF DETECTING ANTIGENIC, NUCLEIC ACID-CONTAINING MACROMOLECULAR ENTITIES

[75] Inventors: Tsanyang Liang, Brookline; Jack R. Wands, Waban, both of Mass.

[73] Assignee: The General Hospital Corporation, Boston, Mass.

[21] Appl. No.: 262,347

[22] Filed: Oct. 25, 1988

[51] Int. Cl.$^5$ ............................................... C12Q 1/70
[52] U.S. Cl. .......................................... 435/5; 435/6; 435/7.1; 435/7.2
[58] Field of Search ..................... 424/12; 435/7, 6, 5; 436/514, 504; 195/103.5; 530/413

[56] References Cited

U.S. PATENT DOCUMENTS 4,271,145  6/1981  Wands ................................... 424/85
4,293,652  10/1981  Cohen .................................. 435/172

FOREIGN PATENT DOCUMENTS 201184  10/1985  European Pat. Off. .
200362  12/1986  European Pat. Off. .
258017  3/1988  European Pat. Off. .

OTHER PUBLICATIONS

Jansen, R. W. et al., *Proc. Natl. Acad. Sci., U.S.A.*, 87: 2867–2871 (1990).
Zeldis, J. B. et al., *J. Clin. Invest.* 84: 1503–1508 (1989).
Liang, T. J. et al., *J. Clin. Invest.* 84: 1367–1371 (1989).
Andrews, W. H. *Food Tech.* 39: 77–82 (1985).
Wands, J. R. et al., *Gastroenterol.* 80:225–232 (1981).
Ben-Porath, E. et al., *Prog. Liver Diseases* 8:347–366 (1986).
Ben-Porath, E. et al., *J. Clin. Invest.* 76:1338–1347 (1985).
Dienstag, J. J. et al., in *Harrison's Prin. Int. Med.* (R. G. Petersdorf et al., ed) 10th ed., 1983 pp. 1789–1801.
Saiki, R. K. *Science* 239:487–491 (1988).
Mullis, K. B. et al., *Meth. Enzymol.* 155:335–350 (1987).
Scharf, S. J. et al., *Science 233:1076–1079 (1986).*
Saiki, R. K. eta l., *Science* 230:1350–1354 (1985).
Kwok, S. et al., *J. Virol. 61:1690–1694 (1987).*
Kaneko, S. et al., *Hepatology* 8:1222 Abstract No. 15 (1988).
Lee, M.-S. et al., *Science* 237:175–178 (1987).
Almoguera, C. et al., *Ccell* 53:549–554 (1988).
Marx, J. L., *Science 240:1408–1410 (1988).*
Li, H. et al., *Nature* 335:414–417 (1988).
Landegren, U. et al., *Science* 242:229–237 (1988).
Ou, C. Y. et al., *Science* 239:295–297 (1988).
Wands et al., *Proc. Natl. Acad. Sci. U.S.A.* 78:1214–1218 (1981).
Miele, E. A. et al., *J. Mol. Biol. 171:281–295 (1983).*
Chu, B. C., *Nucl. Acids Res.* 14:5591–5603 (1986).
Marciniak, R. A. et al., *Proc. Natl. Acad. Sci. U.S.A.* 80: 3821–3825 (1983).
Tiollais, P. et al., *Nature* 317:489–495 (1985).

*Primary Examiner*—Christine Nucker
*Assistant Examiner*—Jeffrey Stucker
*Attorney, Agent, or Firm*—Sterne, Kessler, Goldstein & Fox

[57] ABSTRACT

A method for the detection of nucleic acid-containing moieties is described which combines affinity capture of the moiety with detection and identification of the moiety's nucleic acid.

11 Claims, 4 Drawing Sheets 1 hour (pg) 10  1  $10^{-1}$  $10^{-2}$ $10^{-3}$ $10^{-4}$ $10^{-5}$ $10^{-6}$ —566 bp 3 days (pg) 10  1  $10^{-1}$  $10^{-2}$ $10^{-3}$ $10^{-4}$ $10^{-5}$ $10^{-6}$ —566 bp

METHOD OF DETECTING ANTIGENIC, NUCLEIC ACID-CONTAINING MACROMOLECULAR ENTITIES

The research underlying this patent application was supported by National Institutes of Health Grant CA35711; the Government has certain rights in this invention.

FIELD OF THE INVENTION

The invention relates to a method for the detection of low levels of moieties such as organisms and antigenic, nucleic acid-containing, macromolecular entities. In a specific embodiment, the invention relates to a method for the detection of hepatitis virus which combines immunological capture of viral particles with amplification and identification of viral nucleic acid sequences

BACKGROUND OF THE INVENTION

The rapid detection and identification of medically important organisms and macromolecular entities such as bacteria, viruses, malignant cells and the like is of critical importance in establishing diagnoses, treating patients, tracing the source of infections, detecting biological contaminations, and routinely screening and monitoring blood, tissue banks and food so that public health might not be compromised.

The ability to detect and identify pathogenic organisms and macromolecular entities is limited by the sensitivity and rapidity of the detection system. In addition, identification of pathogenic organisms in blood or tissue samples poses special problems; not only is the availability of sample limited but the concentration of the pathogenic organism in that sample is often very low.

Techniques based on molecular methods of detection such as nucleic acid hybridization, restriction enzyme analysis, Southern analysis, Northern analysis, Western analysis and immunoassay have not overcome the problem of detecting low levels of pathogenic entities in dilute conditions. In many cases it is necessary to first incubate samples suspected of containing a pathogenic organism so as to enrich and increase the number of organisms to identifiable levels before detection and identification is possible. Andrews, W.H., *Food Tech.* 39:77–82 (1985). However, growth and enrichment steps are extremely time-consuming in situations where time is of the essence in establishing the presence or identity of an infectious organism.

In addition, growth requirements for some organisms are very complex and false negatives are a concern. Lack of growth of a bacterium may only indicate that the growth conditions weren't favorable, or that other, nonpathogenic bacteria in the sample grew faster than the organism in question and successfully "competed it out".

Methods for the detection and identification of pathogenic entities such as viruses are even more complex then those for entities like bacteria. More commonly, they depend on the acute and convalescent measurement of a serologic or antibody response to the infectious agent. These measurements are often time-consuming. They often depend on identification and use of a suitable cell line which the virus can infect and in which the virus can replicate. They may also depend on the identification of an animal host which the virus can infect and in which the virus will induce diagnostic serological symptoms.

Thus the identification of a pathogenic organism in blood and tissue samples may be missed even though the organism was present in the sample at levels infectious to humans.

Specific affinity reagents such as high affinity monoclonal antibodies have, in some cases, made it possible to confirm the presence, in blood or tissue samples, of organisms known or suspected of being infectious or otherwise pathogenic. For example, high affinity monoclonal antibodies directed to the hepatitis B surface antigen ($HB_sAg$) have been developed, Wands, J.R., et al., *Gastroenterology* 80:225–232 (1981). These antibodies have successfully identified the presence of hepatitis B virus or its variants in low levels in the blood and tissues of some patients with acute and chronic liver disease but with no known serologic marker of recent or past hepatitis B infection and also in some "healthy" individuals who had no clinical symptoms, Ben-Porath, E. et al., *Progress in Liver Diseases* 8:347–366 (1986); Ben-Porath, E. et al., *J. Clin. Invest.* 76:1338–1347 (1985).

However, studies using a monoclonal antibody have been limited because it has been impossible to further characterize or study the molecular identity of the virus or variant in these patients. Levels of the virus, although detectable with the monoclonal antibody, are often too low for cloning, sequencing and other methods of viral characterization. See, e.g., Dienstag, J.L. et al., in *Harrison's Principles of Internal Medicine.* R.G. Petersdorf et al., eds., tenth edition, 1983, pp.1789–1801, McGraw-Hill, New York, incorporated herein by reference.

Current methods of identifying hepatitis B virus or its variants have depended on in vitro culture of the virus, radioimmunoassay, or genomic type identification after extraction of the viral DNA or RNA. However, for medical screening, diagnostic, or treatment purposes, these techniques do not always provide the necessary sensitivity. Dienstag, J.L., et al., in *Harrison's Principles of Internal Medicine,* R.G. Petersdorf et al., eds, tenth edition, 1983, pp.1789–1801. In addition, methods like radioimmunoassay may non-specifically detect the presence of viral antigens without providing information about the specific subtype.

The polymerase chain reaction (PCR) is a powerful technique for the amplification of specific DNA sequences. Cohen, S.N., U.S. Pat. No. 4,293,652; Erlich, H.A. et al., EP 258,017; Mullis, K.B., EP 201,184; Mullis et al., EP 200,362; Saiki, R.K., et al., *Science* 239:487–491 (1988); Mullis, K.B. et al., *Meth. Enzymol.* 155:335–350 (1987); Scharf, R.K., et al., *Science* 233:1076–1079 (1986) and Saiki, R.K., et al., *Science* 230:1350–1354 (1985).

The polymerase chain reaction technique has the ability to amplify a DNA sequence several orders of magnitude in a few hours, and has been used for the detection of low levels of viral sequences, Kwok, S. et al., *J. Virol.* 61:1690–1694 (1987), including hepatitis B, Kaneko, S., et al., *Hepatology* 8:1222 (1988); cloning of low-abundant DNA sequences, Lee, M.S., et al., *Science* 237:175–178 (1987); detection of malignant cells with chromosomal rearrangements, Lee, M.S., et al., *Science* 237:175–178 (1987); amplification of somatic mutational activation of cellular oncogenes in human tumors, Almoguera, C., et al., *Cell* 53:549–554 (1988); and in the analysis of clinical and forensic samples for the detection and identification of individual DNA genotype, Marx, J.L., *Science* 240:1408–1410 (1988), and haplotype, Li, H. et al., *Nature* 335:414-417 (1988). The use of the polymerase chain reaction as a DNA diagnostic technique has been recently reviewed, Landegren, U., et al., *Science* 242:229-237 (1988), incorporated herein by reference.

The polymerase chain reaction is based on the use of oligonucleotide primers complementary to sequences flanking a particular region of interest for primer-directed DNA synthesis in opposite and overlapping directions. With repeated cycles of high-temperature template denaturation, oligonucleotide primer reannealing, and polymerasemediated extension, DNA sequences can be faithfully amplified several hundred-thousand fold. The amplified sequences are remarkably accurate so one can reliably determine the nucleotide sequences immediately after the polymerase chain reaction.

In theory, only one copy of the target gene need be present in a sample for the polymerase chain reaction to adequately target and amplify it. For example, the polymerase chain reaction amplification technique has been used to analyze the DNA in an individual diploid cell and a single sperm. Li, H. et al. *Science* 335: 414-417 (1988). Ou, C.Y., et al., *Science* 239:295-297 (1988), has suggested the use of the polymerase chain reaction for the detection of HIV-1 virus in DNA from peripheral blood mononuclear cells.

However, use of the polymerase chain reaction is not immediately applicable to all samples. For example, it is not possible to directly test blood or serum using the polymerase chain reaction method because serum contains many inhibitors of the PCR technique. Studies utilizing the polymerase chain reaction to study blood cells have had to first isolate DNA from the cells by phenol or other similar, suitable techniques known in the art for isolation and concentration of DNA. This results in a large loss of sensitivity.

Thus, there remains a need for methodology, applicable to serum and other biological samples, for the rapid identification of low levels of pathological entities. Such would be methodology that does not require DNA isolation or prolonged incubation in vitro, that is sensitive enough to detect the presence of a extremely dilute levels of organisms and macromolecular entities in a sample and which promotes the cloning and genetic analysis of the pathological entity. Such methodology would still be technically simple enough to be embodied as a kit, and amenable for use as a routine screening method.

SUMMARY OF THE INVENTION

The present invention provides a method for the detection and identification of moieties such as antigenic, nucleic acid-containing organisms and macromolecular entities which comprises trapping, concentrating and sequestering the organism or macromolecular entity with an affinity capture reagent and then detecting or identifying said moieties using amplified nucleic acid sequences specific to those moieties.

As an illustration, the present invention provides a method for the detection and identification of hepatitis B virus and its variants which is approximately 1000-fold more sensitive than immunoanalysis alone and comprises immunological capture and concentration of hepatitis B virus particles using high affinity monoclonal antibodies and amplification of specific, hepatitis B target genomic loci using the polymerase chain reaction.

BRIEF DESCRIPTION OF THE DRAWINGS

FIG. 1 is a Southern analysis which shows the sensitivity of the polymerase chain reaction after 25 cycles for detection of hepatitis B virus DNA.

DETAILED DESCRIPTION OF THE INVENTION

Figure 1A:
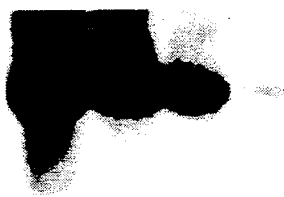
FIG. 1A is a one hour exposure of the autoradiography and FIG. 1B is a three day exposure of the same autoradiography. The picograms (pg) of virus detected by the signal is placed above each lane.

The invention provides a sensitive and specific method for the detection and identification of nucleic acid-containing moieties which comprises high-affinity capture of such moiety and analysis of macromolecular entity-specific nucleic acid in such moieties.

This method is capable of detecting and identifying low levels of biological organisms such as bacteria, viruses, parasites, and the like, from serum and other biological sources.

For example, this method is capable of concentrating, detecting and identifying extremely low levels of hepatitis B virus or its variants in serum.

In detail, the invention provides a method of isolating and identifying nucleic acid-containing moieties, such as organisms and macromolecular entities by, first, isolating, concentrating, and sequestering the moiety from the sample milieu. The isolation, concentration, and sequestration is achieved with an affinity reagent such as a high affinity monoclonal antibody. The trapped moiety may then be lysed, its DNA is denatured, and defined regions of genomic or other nucleic acid sequences associated with the entity detected or identified or otherwise characterized using amplified nucleic acid sequences specific to a known DNA.

Consequently, the invention embraces any method which uses a combination of affinity capture and nucleic acid analysis to extract, concentrate, amplify, characterize and/or identify nucleic acidcontaining organisms or macromolecular entities.

DESCRIPTION OF THE PREFERRED EMBODIMENTS

The invention is originally based on the inventors' surprising discovery that unprecedented levels of sensitivity and speed of hepatitis B virus or variant detection are achieved when a) solid phase, high affinity monoclonal antibodies to hepatitis B surface antigens are used to extract, concentrate, immobilize and sequester hepatitis B particles from serum, in a manner which allows extraction and isolation of the virus away from nondesirable components present in serum, and in a manner which allows recovery of the virus and subsequent analysis of its DNA with the polymerase chain reaction.

The present invention offers an objective method of screening, concentrating, characterizing, identifying, sequencing and/or cloning low levels of any organism or macromolecular entity which is capable of capture with a specific capture reagent and which also is capable of providing DNA for in vitro amplification.

DEFINITIONS

In order to provide a clear and consistent understanding of the specification and claims, including the scope to be given such terms, the following definitions are provided.

Macromolecular entity. The term "macromolecular entity" is intended to refer generally to any biological entity which is synthesized in, replicates in, or is extractable from, a biological source such as a microbe, plant, animal or the tissues thereof. Examples of macromolecular entities within the meaning of this word include infectious agents, bacteria, viruses, protozoans, pneumocystises, mycoplasma, parasites, fungi, molds, yeast or microbes. In some cases, a subcellular macromolecule or complex thereof may also be considered to be a macromolecular entity within the meaning of the invention. For example, a nucleic acid which is also antigenic, either due to the presence of a protein or other antigenic material bound to the nucleic acid, or to an inherent antigenicity in the nucleic acid itself which allows it to be recognized by an antibody or other high affinity capture reagent, would be considered a macromolecular entity within the meaning of the invention.

Capture Reagent. The term "capture reagent" is intended to refer generally to a biological entity which has the inherent ability to bind to, and thus form an affinity with, a specific macromolecular entity. Capture reagents include polyclonal and monoclonal antibodies, receptor molecules, protein A, hormones, enzymes, desialylated glycoproteins, lectins, toxins, and the like. Organisms such as bacteria and viruses may, in certain instances, serve as capture reagents if they specifically interact with a unique target, such as a membrane receptor.

The method of the invention is applicable to the use of a virus or other organism as a capture reagent to extract and concentrate cells or other macromolecular entities containing organism-specific receptors; the identity of the captured cell would then be determined by its genotype upon amplification of its DNA.

The type of organism or macromolecular entity which is capable of being extracted, concentrated, purified, characterized, cloned, identified or otherwise analyzed by the method of the invention is limited only a) by the identification of a specific capture reagent possessing an inherent affinity for and an ability to extract the macromolecular entity from the milieu in which it is found; and b) by the identification of nucleic acid sequences which can be used to target specific sequences in the macromolecular entity for amplification.

The organism or macromolecular entity need only be nucleic acid-containing, not necessarily double-strand DNA (dsDNA)-containing. Macromolecular entities that contain nucleic acid other than dsDNA, such as single-stranded (ss) RNA, ssDNA, dsRNA, or mRNA are capable of analysis by the method of the invention. For example, to amplify nucleic acid sequence information by the polymerase chain reaction, which requires dsDNA, moieties containing nucleic acid in a form other than dsDNA can be subjected to an intermediate step(s) in which the ssRNA, ssDNA, dsRNA or mRNA is converted to the dsDNA form.

For example, viruses containing ssDNA genomes can be converted to dsDNA with DNA polymerase I; viruses containing ss or dsRNA genomes can be converted to a dsDNA form by reaction with reverse transcriptase and DNA polymerase I. It is not necessary to transcribe the entire genome into dsDNA, rather the probes designed for use in the polymerase chain reaction can be used to prime the transcription of only a region of interest.

Use of reverse transcriptase and DNA polymerase I to synthesize dsDNA from ssRNA or ssDNA templates is well known in the art, Maniatis, T., et al., *Molecular Cloning (A Laboratory Manual)*, Cold Spring Harbor Laboratory, 1982. This advantage has recently been recognized by others, Li. H. et al., *Nature* 335:414-417 (1988); and Mullis, K.B., EP201,184.

Alternatively anti-sense RNA can be used to convert ssRNA to a double-stranded form, Lichtenstein, C. *Nature* 333:801 (1988).

In a preferred embodiment, the capture reagent used to extract the macromolecular entity is a monoclonal antibody, bound to a solid phase support. The sample is placed in contact with a monoclonal antibody on the solid phase support and the material, if desired, is incubated for a defined time, such as several hours or overnight. The desired time of incubation is that time required for affinity capture to be essentially complete. The temperature of this capture may be any temperature which permits affinity capture to occur in the desired time, usually room temperature. The solid phase supports are then extensively washed with an appropriate physiological buffer, for example, a phosphate buffered saline solution at a physiological pH, and the captured sample used as a substrate for analysis with nucleicacid amplification methodology.

In a preferred embodiment, the capture reagent bound to the solid phase support is used in the analysis of serum or other biological fluid or tissue for the presence of a pathogenic organism, eukaryotic cell or other macromolecular entity. The advantage of this method for the analysis of serum and other milieu which contain components inhibitory to the polymerase chain reaction is that it isolates and concentrates the macromolecular entity, in a highly specific manner, in one step, away from the milieu, leaving the macromolecular entity intact but sequestered, trapped and locatable on a matrix and now amenable to other techniques.

In an illustrative preferred embodiment, high affinity monoclonal antibody 5D3 is bound to a solid phase and used to assay for the presence of hepatitis B antigen or its variants in serum. The cell line producing 5D3 was deposited with the American Type Culture Collection, 12301 Parklawn Drive, Rockville, MD 20852, USA, on Aug. 25, 1988, and was assigned ATCC No. HB9801. Reference to antibody 5D3 is made in U.S. Pat. No. 4,271,145, issued to Wands et al.. as well as in Wands et al., *Proc. Natl. Acad. Sci. USA* 78:1214-1218 (1981), both incorporated herein by reference.

Affinity capture of the organism or other macromolecular entity on a solid support is advantageous as a first step in the method of the invention because it eliminates volume of the sample, or a dilute concentration of the macromolecular entity, as being factors limiting the sensitivity of the invention. Affinity capture also eliminates the need for bulk in vitro extraction of DNA from serum samples or other samples containing inhibitors of the polymerase chain reaction prior to amplification analysis. The affinity capture step eliminates the need for preliminary growth, enrichment, or culture of samples to increase the numbers of organisms present to detectable levels. In addition, affinity selection provides a way to control the specificity of the analysis in a manner independent from the nucleic acid amplification and in a manner which does not necessarily adversely adulterate or otherwise harm the sample being tested. That is, by using affinity capture as a first step, the integrity of the non-extracted components in the sample is maintained. After affinity selection, the sample can be used in other assays.

The volume of the substance being tested for the presence of the macromolecular entity can be expanded to include any volume desirable, as long as the affinity capture reagent has access to that volume. Such access may be achieved for example, by passing the volume of the substance being tested through a column containing the affinity capture reagent or through a filter containing the affinity capture reagent or by the passing a dipstick containing the bound capture reagent through a solution of the substance being tested.

The volume of a substance required for the analysis is a function of the affinity of the capture reagent for the organism or macromolecular entity to be captured and the expected concentration of organism or macromolecular entity in the substance. The partial amino acid or nucleic acid sequence of the organism or macromolecular entity, however, must be known to prepare oligonucleotide primers or probes of defined sequences.

In another embodiment, the capture reagent is not bound to a solid phase support when it captures the organism or macromolecular entity, but is subsequently extracted and sequestered onto a solid phase, for example, by using filtration to deposit affinity-captured moieties on a filter or, for example, by using a second affinity agent to recover the captured moieties wherein the second affinity agent is bound to a solid phase.

The affinity capture reagent may be specific for one moiety in the sample or it may comprise a mixture of affinity reagents with differing specificity. Mixtures of affinity capture reagents may comprise mixtures wherein each reagent is directed to different affinity targets on the same moiety; or it may comprise a mixture wherein each affinity reagent is directed to a different moiety. In the latter example, the capture step recovers a group of different moieties in one step. Alternatively, the sample may be repeatedly exposed to a series of capture and extraction steps, each step extracting and isolating a different moiety in the sample.

Any appropriate geometry of solid phase support can be used as the backbone upon which to present the capture reagent to the macromolecular entity such as latex beads, membranes, dipsticks, microtiter dishes, and the like.

Dipstick-bound capture reagents present the advantage of being applicable to capturing a macromolecular entity whether it is in solution or in a solid phase. For example, a dipstick can be passed through a solution. Alternatively, the dipstick may be placed in contact with the substance being tested, for example, by laying the dipstick on the top of a gel, blood smear, or tissue section.

In a preferred embodiment, the capture reagent is covalently bound to a bead and mixed with a solution containing the organism or macromolecular entity. After binding the entity, the beads are recovered by centrifugation and washed by resuspension and recentrifugation.

In another embodiment, affinity chromatography using high affinity monoclonal antibodies is utilized for the capture, purification and concentration of the macromolecular entity.

The source of the antibodies may be homologous with that of the macromolecular entity. For example, monoclonal antibodies to a hepatitis B virus envelop protein can be used for the extraction of any hepatitis B virus or variant that is present. Alternatively, the macromolecular entity may be heterologous to the source of the antibodies, for example, monoclonal antibodies to membrane proteins found in one type of cell can be used for the specific extraction of those cells. Cells sequestered in this manner can then be analyzed for the presence of a second entity, such as an integrated virus in said cells.

It is important that the affinity between the macromolecular entity and capture reagent be high enough to a) recognize and bind the macromolecular entity even in a very dilute biological milieu and b) withstand washing of the macromolecular entity-capture reagent complex to remove non-bound serum components.

Washing is accomplished by rinsing the solid phase bound macromolecular entity-capture reagent complex with an appropriate salt solution to promote the dissociation of components nonspecifically retained on the solid matrix, while maintaining the requestration, that is, interaction between the macromolecular entity and capture reagent.

Appropriate washing solutions include any solution which promotes dissociation of non-specifically bound substances while not promoting the dissociation of the specific complex between the capture reagent and the macromolecular entity. Nucleic acid liberated from the captured macromolecular entity by heating at a high temperature is used as a substrate for amplification and analysis. If the capture reagent is a high affinity monoclonal antibody, solutions such as 0.9% NaCl, phosphate-buffered saline, or even water, are appropriate.

The captured nucleic acid must be released from the bound organism or macromolecular entity and denatured before it can be used, amplified or otherwise analyzed.

In a preferred embodiment, the release of the captured DNA occurs concurrent with the first denaturation step in the polymerase chain reaction. For example, beads containing the captured organism are added directly to the polymerase chain reaction mixture. The sample is then heated to a temperature sufficient to both release DNA from the organism and to denature it, such as 94° C. for 1 minute and typically 80°-105° C. for 1-10 min. The remaining steps of the polymerase chain reaction are not altered. The sample is cooled to the desired annealing temperature for a time sufficient to allow the primers to anneal to the template, and then heated for the desired time at the temperature desired for the primer extension step. The temperature and time of annealing and extension are a function of primer composition and size and are well known to those in the art. See, e.g., Szostak, J.W., et al., Meth. Enzymol. 68:419–428 (1979); *Nucleic Acid Hybridization.* B.D. Hames and S.J. Higgins, eds., IRL Press, Washington, D.C., 1985; and Hamley, P. et al., *J. Biochem.* 254:4876 (1979). Automated embodiments capable of repeated cycles through the denaturing, annealing and extension temperatures greatly simplify the procedure and are available as the "DNA thermocycler" from Perkin Elmer Cteus, Landegren, U., et al., *Science* 242:229-237 (1988).

The primers can be prepared by any suitable method such as phosphotriester and phosphoester diester methodology. Mullis, K.B., EP 201,184; Beaucage, et al., *Tetrahedron Lett.* 22:1859-1862 (1981); and U.S. Pat. No. 4,458,066. The primer may be added to the reaction with a group of different primers, each designed to hybridize with a different target.

Methods for the annealing and extension by primer extension F methodology are described in Cohen, S.N., U.S. Pat. No. 4,293,652; Erlich, H.A. et al., EP 258,017; Mullis, K.B., EP 201,184; Mullis et al., EP 200362; Saiki, R.K., et al., *Science* 239:487-491 (1988); Mullis, K.B. et al., *Meth. Enzymol.* 155:335-350 (1987); Scharf, R.K., et al., *Science* 233:1076-1079 (1986) and Saiki, R.K., et al., *Science* 230:1350-1354 (1985).

Extension of the template in the polymerase chain reaction preferably is performed with a heat stable polymerase, for example, the thermostat polymerase from *Thermus aquaticus*, Saiki, R.K. et al., EP258,017.

Methods to detect, analyze, sequence or clone the amplified macromolecular entity sequence include those conventional in the art of nucleic acid analysis, sequencing and cloning. Maniatis, T. et al., *Molecular Cloning (A Laboratory Manual)*, Cold Spring Harbor Laboratory (1982); and Landegren, U., et al., *Science* 242:229-237 (1988).

Detection methods include isotopic, fluorescent, chemiluminescent, immunoreactive or colormetric techniques.

For example, the amplified sequences may be labeled with a suitable radioactive label, including $^{32}P$, $^{3}H$, $^{14}C$, $^{35}S$, $^{125}I$, or the like. Any radioactive label may be employed which has a sufficiently long half-life. Transcribed regions may be radioactively labeled, for example, by "nick-translation" by well-known means, as described in, for example, Rigby, P.J.W., et al., *J. Mol. Biol.* 113:237 (1977), or detected after hybridization to a radiolabelled probe.

Alternatively, the detection methodology may be based on a detection of biotinated probes using alkaline phosphatase. Singer, R.H. et al., *BioTechniques* 4:230-249 (1986), avidin and $\beta$-galactosidase, Nagata, Y., et al., *FEBS Lett.* 183:379-382 (1985) or aviden and biotin-specific antibodies, Ward, EP63,879.

Use of nucleic acid sequence information to detect or identify a moiety means the use of any technique ultimately dependent upon a step in the technique which requires nucleic acid hybridization or the lack thereof, for example with a primer or probe, to establish whether nucleic acid sequence similarity exists between the hybridizing nucleic acid and the sample.

The sequence information contained in the amplified macromolecular entity can also be evaluated using conventional restriction enzyme techniques, gel chromotraphy or dot blot analysis.

The nucleic acid captured by the affinity matrix can be analyzed by any method sensitive enough to ultimately produce a detectable result. Landegren, U., et al., *Science* 242:229-237 (1988). For example, probes synthesized and amplified by Q-beta replicase methodology may be used to characterize the nucleic acid of the trapped sample, with or without previous amplification of the sample's nucleic acid by other means. Miele, E.A., et al., *J. Mol. Biol.* 171:281-295 (1983); Chu, B.C., *Nucl. Acids Res.* 14:5591-5603 (1986). Other applicable technologies for the detection and analysis of the captured moiety's nucleic acid include the use of allele-specific nucleotide probes, Conner, B.J. et al., *Proc. Natl. Acad. Sci. USA* 80:278(1983); the oligonucleotide ligation assay, Landegren, U. et al., Science 241:1077 (1988); RNase A, Myers, R.M. et al., *Science* 230:1242 (1985); denaturing gradient gels, Myers, R.M. et al., *Nature* 313:495 (1985) and chemical cleavage, Cotton, R.G.H. et al., *Proc. Natl. Acad. Sci. USA* 85:4397 (1988). The advantages and applications of these techniques have been recently reviewed. Landegren, U. et al., *Science* 242:229-237 (1988).

An advantage of the method of the invention is that the specificity of the method of the invention can be controlled at any of several steps: at the affinity capture step, or at the nucleic acid amplification step, or at the analysis step, or all three. For example, affinity capture using an antibody designed to capture all members of a certain class of virus can be coupled with nucleic acid amplification using primers or probes specific for a certain subclass of virus. Alternatively, primers or probes designed to amplify all members of a given class can be used and the identification of the subclass made on secondary characterization of the amplified nucleic acid, for example, by restriction enzyme analysis or sequencing.

The method of the invention is applicable to the detection and analysis of any virus such as hepatitis virus, picornavirus, retrovirus, reovirus, togavirus, orthomyxovirus, paramyxovirus, rhabdovirus, arenavirus, coronavirus, bunyavirus, papovirus, parvovirus, adenovirus, herpetovirus, or poxvirus, and especially hepatitis B, Non-A, Non-B hepatitis virus, HIV-1, HIV-2, HTLV-1, HTLV-2, human papilloma virus, Epstein-Barr virus, or herpes simplex virus.

The method of the invention is also applicable to the detection of any species of microbe such as *N. gonorhea. Chlamydia T, Candida A, Pneumocystis carinii, E. coli* and the like.

The method of the invention is also applicable to the isolation and detection of low levels of malignant, transformed, tumorigenic or otherwise abnormal cells from biological fluids or tissues, especially, biopsy samples, where it would be desirable for an evaluation of the malignancy of a lesion or tissue or the patient's prognosis.

Examples of biological fluids, solids, or tissues assayable by the methods of the invention include serum, blood, blood cells, sputum, stool, saliva, urine, mucus, pus, warts, moles, and biopsy and tissue samples.

The method of the invention is especially useful for the monitoring of environmental air and water quality and the like, by placing a trap containing the capture reagent on a removable, replaceable solid phase, in-line with the air or water supply.

Having now generally described this invention, the same will be better understood by reference to certain examples which are included herein for purposes of illustration only and are not intended to be limiting unless otherwise specified.

EXAMPLE 1

Rapid Detection of Hepatitis B Virus and its Variants a) Preparation of the Capture Reagent Monoclonal antibody 5D3 has previously characterized as being directed against the surface antigen of hepatitis B ($HB_sAg$) and as having an affinity constant for its antigenic determinant on HB$_s$Ag of $4 \times 10^{11}$ liters/mole per molecule. Wands, J.R., et al., *Gastroenterology* 80: 225-232 (1981). Antibody 5D3 recognizes all known subtypes of HB$_s$Ag and by definition recognizes a part of the a domain of the virus. Ben-Porath, E. et al., *J. Clin. Invest.* 76:1338-1347 (1985). The antibody was coupled to activated CNBr Sepharose beads at a protein concentration of 1 mg to 1 ml of Sepharose slurry as described in Ben-Porath, E. et al., in *Progress in Liver Diseases*, vol. VIII, H. Popper and F. Shaffner, eds., Grune & Stratton, New York, 1986, pp. 403-427, and Marciniak, R. et al., *Proc. Natl. Acad. Sci. USA* 80: 3214-3219 (1983).

b) Incubation of the Capture Reagent with the Sample

Twenty-five microliters of Sepharose-coupled antibody slurry was added to 200 µl of serum and mixed overnight at 37° C. Serum was then decanted after a short centrifugation step. The antibody-Sepharose coupled beads were washed 6 times with phosphate buffered saline by suspension and repelleting to remove serum components from the antigen-antibody complex. The final Sepharose pellet which contains the bound HB$_s$Ag-associated particles, including virons with hepatitis B virus or its variants, was used directly in the polymerase chain reaction.

c) Selection of the DNA Probe Sequences

A computer analysis of known HBV DNA sequences was performed to search for regions of maximal homology representing functional and structural conservation, as well as significant heterogeneity suggesting evolutionary divergence. Since HBV strains from different parts of the world are known to contain significant heterogeneity, Tiollais, P. et al., *Nature* 317:489-495 (1985); Seeger, C. et al., *J. Virol.* 51: 367-375 (1984), and these HBV-related macromolecular entities may harbor DNA sequences significantly different from that of HBV, careful selection of primer sequences was important.

A comparison of all the known DNA sequences of hepadenoviruses, including all the known HBV subtypes, ground squirrel hepatitis virus, (GSHV), woodchuck hepatitis virus (WHV), and duck hepatitis (DHV) was conducted for consensus sequences. Two stretches of nucleotides flanking the hepatitis core gene were identified that had remarkable conserved sequences. The first sequence is in the pre-core region and the other is in the 3' terminus of the core gene. The oligonucleotides representing these two regions are:

Oligo 1 (bases 1865-1889): 5' TTCAAGCCTCCAAGCTGTGCCTTGG 3'

Oligo 2 (bases 2430-2410): 5' TCTGCGACGCGGCGATTGAGA 3'

PROBE (bases 1892-1906): 5' GGCTTTGGGGCATGGACATTGACCC 3'

The first nucleotide spans position 1865 to 1889 (adw subtype), Ben-Porath, E., et al., *J. Clin. Invest.* 76:1338-1347 (1985). Its sequence is 100% conserved in the pre-core region of all known hepadenoviruses. The second oligonucleotide from position 2410 to 2430 also contains sequences which are generally conserved except in WHV and GSH which have a C to T transition at nucleotide position 2418, Seeger, C. et al., *J. Virol.* 51: 367-375 (1984). The third oligonucleotide from position 2269 to 2288 between the two primers (oligo 1 and 2) is also well conserved and will be used as the probe for the amplified fragment. These two oligonucleotide primers will direct and amplify the synthesis of a 566-bp fragment in the polymerase chain reaction. The two oligonucleotide primers were synthesized using Applied Biosystem's DNA Synthesizer. The full-length oligonucleotides (25-mer for first and 21-mer for second oligonucleotide) were purified on preparative denaturing polyacrylamide gel electrophoresis away from shorter sequences resulting from incomplete synthesis. The purified oligonucleotides have been shown to be homogeneous with correct length, free of other oligonucleotides on denaturing polyacrylamide gel. Preliminary results have shown that these two oligonucleotide primers bind specifically to the correct position on HBV DNA and are capable of directing DNA synthesis in the polymerase chain reaction.

Other sequences of homology in the HBV genome have been examined and several oligonucleotide primers in other regions of interest such as in the pre-S and S domains have been selected. By comparison of available nucleotide sequences from different HBV subtypes (adw, adr, ayw) different sets of conserved DNA sequences to be used as primers can be defined. Each primer carries a restriction enzyme site at its 5' end for subsequent cloning.

The nucleotide sequences of five sets of the selected primers spanning the entire S region and cloning sites (bold faced type are mismatched and the underlined sequences are the restriction enzyme site) are presented below:

1)
```
   Hind III                                    Xho I
5'-TGAAGCTCACCATATTCTTGGGAACAAGA-3'    5'CTCTCGAGTAGGCTGCCTTCCTGACTG-3'
     /                        /              /                    /
   3151                     3132           2825                 2847
```

2)
```
   Bam HI                                     Sac I
5'-ATGGATCCTCCTGCCTCCACCAATCG-3'    5'-CTGAGCTCTGCGGTATTGTGAGGATTCTTGTCA-3'
     /                   /              /                          /
   3111                3130           248                         221
```

3)
```
   Sac I                                      Xho I
5'-CCGAGCTCGTGTTACAGGCGGGGTTTTTCTTGT-3'    5'-AACTCGAGGCATAGCAGCAGGATGAAGAGGAA-3'
     /                          /              /                         /
   193                        220            429                        403
```

4)
```
   Bam HI                                     Bgl II
5'-ATGGATCCTGGTTATCGCTGGATGTGTCTGCGG-3'    5'-AAAGATCTGAGGCCCACTCCCATAGG-3'
     /                          /              /                   /
   363                        390            658                  639
```

```
          Xba I                                        Hind III
5'-CGTCTAGAAATTGCACCTGTATTCCCATCCCATC-3'   5'-GTAAGCTTAGGGTTTAAATGTATACCCA-3'    5)
      /                              /         /                          /
     589                            617       844                        823
``` d) Use of the Probes in the Polymerase Chain Reaction to Amplify Captured HBV and/or Variant DNA Sequences The viral particles must first be denatured to expose their DNA to the primers. This is accomplished by running the initial polymerase chain reaction step at a minimum of 80° C.

Amplification of DNA sequences using the polymerase chain reaction and heat-stable polymerase from Thermus Aquaticus (Taq polymerase) has been described elsewhere, Chien, A. et al., *J. Bacteriol.* 127:1550-1557 (1976); Saiki, R.K. et al., *Science* 230: 1350-1354 (1988). The method is a modification of the procedure described by Saiki, supra. DNA was amplified in a 50 μl reaction volume containing 25 pmole of each oligonucleotide primer in 1x reaction buffer [10 mM Tris-Cl pH 8.3, 50 mM KCl, 1.5 mM MgCl2, 0.01% (w/v) gelatin, 200 mM of dATP, dGTP, dCTP, TTP each and 0.25 units of Taq polymerase (Cetus)]. Reaction mixtures were overlaid with 30 μl of mineral oil to prevent evaporation. Samples were heated at 94° C. for 1 minute to denature the DNA, placed at 45° C. for 2 minutes to allow primers to anneal to the template, then transferred to 72° C. for 3 minutes for primer-directed DNA synthesis. Subsequent rounds consisted of repeated cycles of the denaturing step described above at 95° C., cool-down at 45° C. and an extension step at 72° C. On the average, 25 to 35 rounds performed in this manner.

The amplified samples were analyzed either by direct spotting of an aliquot to nylon membrane for DNA dot-blot hybridization or on agarose gel to visualize the amplified fragments by ultraviolet light fluorescence after staining with ethidium bromide, or, by direct probing with a subgenomic fragment of HBV-DNA or by a defined oligonucleotide sequence within the amplified DNA (see below).

e) Comparison of the Sensitivity of Hepatitis B Virus Detection using only the Polymerase Chain Reaction or using Monoclonal Antibody Capture plus the Polymerase Chain Reaction.

Figure 1B:
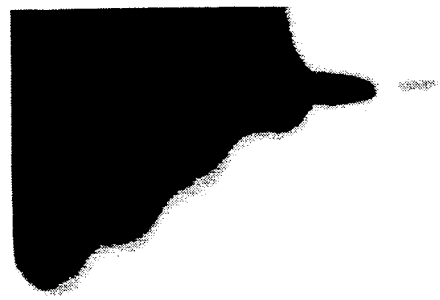

As is shown in FIG. 1, using only the polymerase chain reaction to detect hepatitis B virus in a serum sample, the sensitivity of detecting a 566 bp transcript following 25 rounds of amplification was $10^{-5}$ pg HBV DNA by hybridization; (it was only $10^{-2}$ pg HBV DNA by ethidium bromide staining of agarose gels). It is noteworthy that $10^{-5}$ pg of HBV DNA correspond to 3 molecules of HBV genome. Continuing the PCR beyond 25 cycles will amplify DNA even further; $10^{-5}$ pg of HBV DNA can be detected by ethidium bromide staining after 35 rounds of PCR, reflecting an amplification magnitude of $>10^9$.

Figure 2:
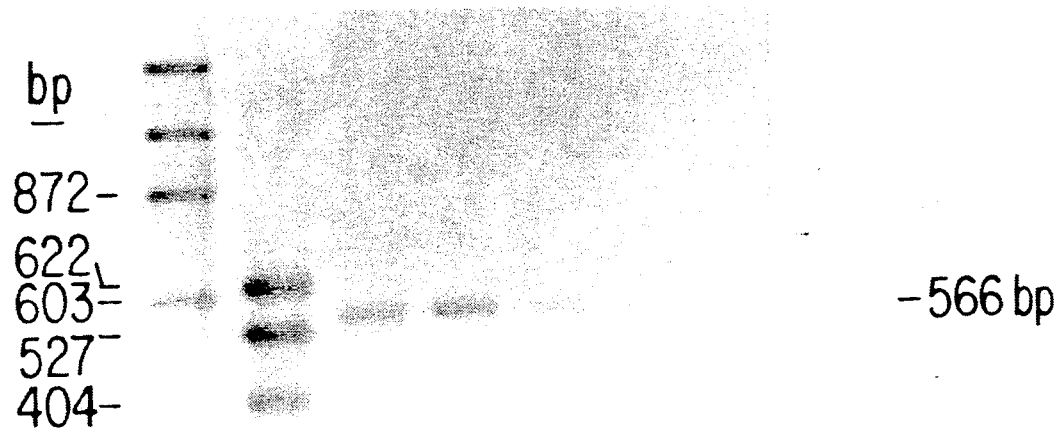
FIG. 2 is a Southern analysis showing the sensitivity of the combination of monoclonal antibody capture and 35-cycle polymerase chain amplification as compared to immunoassay by the M-IRMA technique. The dilution of the serum and results of the M-IRMA analysis are placed at the top of each lane. Lanes 1 and 2 represent standards used for molecular weight markers.
Figure 3:
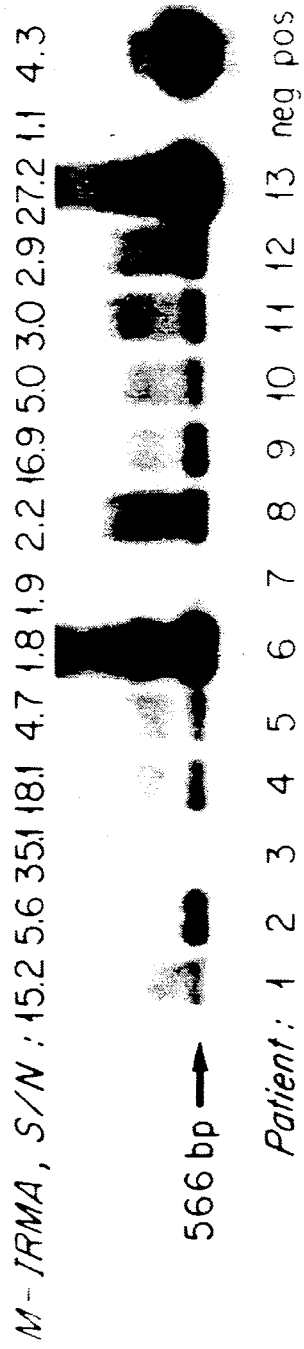
FIG. 3 shows the detection of hepatitis B virus DNA sequences in patients with chronic liver disease.
Figure 4:
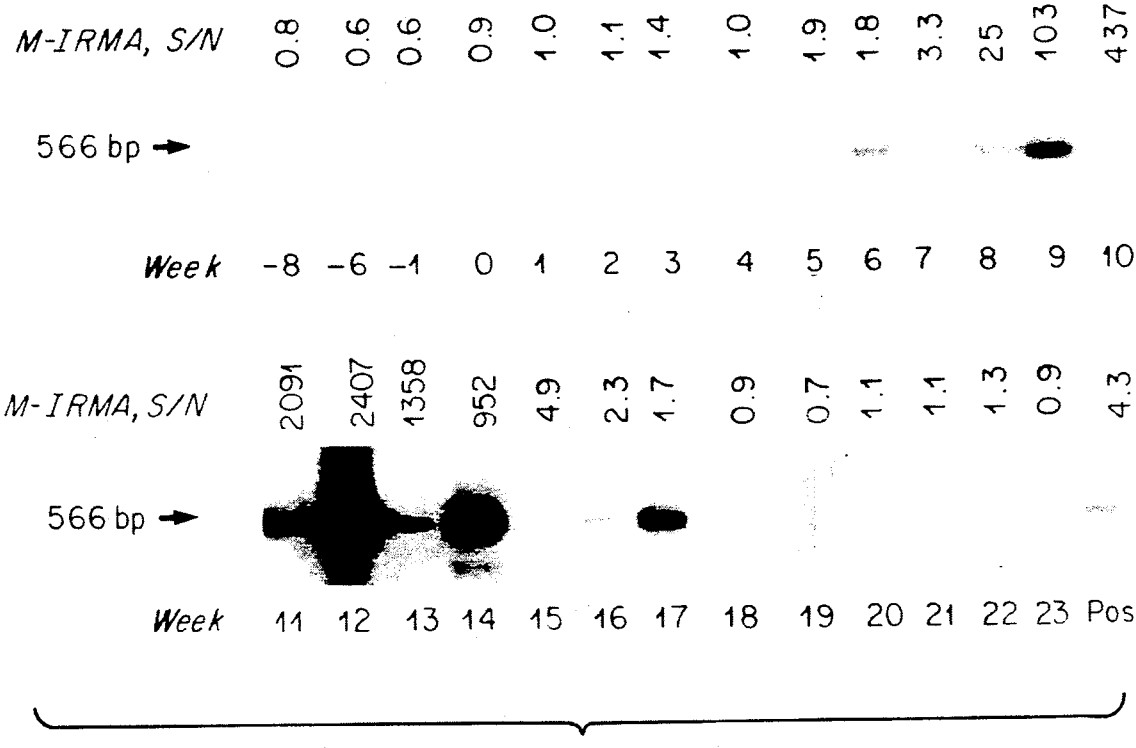
FIG. 4 shows the detection of hepatitis B virus DNA sequences in a chimpanzee inoculated with serum derived from a patient tentatively diagnosed as having chronic Non-A, Non-B hepatitis.

FIG. 2 demonstrates the sensitivity of the monoclonal antibody capture system when it is combined with the polymerase chain reaction. Serum from a patient who was reactive by both the M-IRMA immunoassay (Ben-Porath, E. supra) and DNA hybridization (dot blot technique) was serially diluted. Binding of the monoclonal M-IRMA assay was compared to the polymerase chain reaction assay following capture with the monoclonal anti-HBS IgM linked to a solid phase support. A positive result in the M-IRMA assay is a S/N value of greater than 2. As is shown in FIG. 2, at a dilution between $10^{-4}$ and $10^{-5}$ the M-IRMA becomes negative. However, by the technique of the invention, that is, by using the polymerase chain reaction to amplify the DNA captured by the monoclonal antibody, a serum dilution of $10^{-7}$ is easily detectable. This indicates that the combination of antibody capture with the polymerase chain reaction amplification step is approximately 1000-fold more sensitive for detection of the hepatitis B virus or its variants in serum from a patient than the immunoassay.

f) Detection of Hepatitis B Virus DNA Sequences By Monoclonal Antibody IgM Capture followed by Polymerase Chain Reaction Amplification in Patients with Chronic Liver Disease (Patients were examined who had been diagnosed as having chronic liver disease but in whom conventional hepatitis B virus marker (anti-HBcAG, anti-HB$_s$Ag and HB$_s$Ag) was not detected by commerical assay (AUSAB, CORAB, and AUSRIA II, Abbott Laboratories). Two patients who did test positive by commercial assays for one of the markers were also examined: patient number 11 tested positive for anti-HBcAG and patient number 12 tested positive for anti-HB$_s$Ag. The serum from all patients was tested by dot blot hybridization against a hepatitis B virus probe and found to be negative. The serum from all patients was also tested by immunoassay as described in Ben-Porath, E., supra, for the presence of HB$_s$Ag associated epitopes by M-IRMA. FIG. 3 shows the results of the M-IRMA assay and the capture/amplification assay. Amplified DNA was electrophoresed on agarose gels, transferred to nylon membranes and hybridized with $^{32}$P-hepatitis B virus DNA. The last two lanes in the figure represent negative and positive controls, respectively. As shown in FIG. 3, all of the patients were clearly identified as being hepatitis B carriers by the method of the invention. Some of these patients, for example patient Nos. 6 and 7, had been missed by the M-IRMA assay.

g) Detection of Hepatitis B Virus DNA by Monoclonal Antibody Capture Followed by Polymerase Chain Amplification in a Chimpanzee Undergoing Experimental Infectivity Studies with Hepatitis B virus A chimpanzee was inoculated with serum derived from a patient with presumed chronic Non-A, Non-B hepatitis (patient number 9 in FIG. 3). This patient's serum was reactive for HB$_s$Ag-associated epitopes only by M-IRMA and was negative for all other hepatitis B virus associated serologic markers. The chimpanzee was bled weekly and his serum analyzed for HB$_s$Ag associated epitopes by M-IRMA and for hepatitis B virus sequences by monoclonal anti-HBs IgM capture followed by polymerase chain amplification. As is shown in FIG. 4, the method of the invention detected the virus in the chimp's serum before it was detected by either M-IRMA or by hepatitis B virus DNA hybridization by dot blot techniques.

During these experimental infectivity studies in a chimpanzee, hepatitis B virus DNA was detected by the monoclonal capture technique of the invention four weeks after inoculation. This was earlier that the appearance of the HB$_s$Ag marker as detected by M-IRMA. Even in the presence of low titer anti-HBs at week 17, hepatitis B virus DNA was still detectable in serum by the method of the invention. Importantly, hepatitis B virus was still being detected by the method of the invention after clearance of the virus had been indicated by the M-IRMA technique. This indicates that hepatitis B virus remains in the blood for a longer period of time than previously recognized. These results demonstrate that this technique is much more sensitive for the detection of virus that either M-IRMA or dot blot analysis.

h) Cloning of DNA Captured by the Antibody-Amplification Technique

After 35 cycles of amplification, enough DNA is available for digestion and cloning with appropriate restriction enzymes. The amplified DNA sequences can be cloned in TGI bacteria after insertion in bacteriophage M$_{13}$mp18 and M$_{13}$mp19 to obtain both orientations of the insert. The phage containing recombinants can be detected using an internal oligonucleotide as a probe. Single strand M13 recombinant DNA will be prepared and sequencing performed using the dideoxy extension method.

Now having fully described this invention, it will be understood by those with skill in the art that the scope may be performed within a wide and equivalent range of conditions, parameters, and the like, without affecting the spirit or scope of the invention or of any embodiment thereof.

What is claimed is:

1. A method for the detection or identification of an antigenic, nucleic acid-containing, macromolecular entity which comprises the steps of:
   a. affinity capturing the macromolecular entity from the sample being tested and
   b. detecting or identifying said macromolecular entity using amplified nucleic acid sequence specific to said macromolecular entity.

2. The method of claim 1, wherein said macromolecular entity is a virus.

3. The method of claim 1, wherein said macromolecular entity is a malignant, transformed, or abnormal human cell.

4. The method of claim 1, wherein said affinity capture is with an antibody.

5. The method of claim 4, wherein said antibody is a monoclonal antibody.

6. The method of claim 5, wherein said antibody is directed against hepatitis B virus.

7. The method of claim 6, wherein said antibody is that obtained from cell line ATC HB9801.

8. The method of claim 1, wherein said amplification is through the polymerase chain reaction.

9. The method of claim 1, wherein said sample being tested is serum.

10. The method of claim 1, wherein said sample being tested is blood or blood cells.

11. A method for the detection of hepatitis B virus or its variants which comprises,
   immunologically extracting said virus with a solid-phase-bound monoclonal antibody,
   lysing the viral protein coat to expose said virus' DNA,
   detecting or identifying said virus using nucleic acid sequence information from hepatitis B or its variants and
   relating said DNA to the presence or absence of said hepatitis virus or its variants.

* * * * *

UNITED STATES PATENT AND TRADEMARK OFFICE
CERTIFICATE OF CORRECTION

PATENT NO. : 5,077,192
DATED : December 31, 1991
INVENTOR(S) : Liang et al.

It is certified that error appears in the above-indentified patent and that said Letters Patent is hereby corrected as shown below:

Column 1, line 25, "source" is incorrect and should be replaced with --sources--;

line 45, "is" is incorrect and should be replaced with --are--; and line 59, "then" is incorrect and should be replaced with --than--.

Column 2, line 3, "was" is incorrect and should be replaced by --is--; and line 22, "a monoclonal antibody" is incorrect and should be replaced with --monoclonal antibodies--;

line 34, "in vitro" is incorrect and should be replaced by --*in vitro*--;

Column 3, line 24, "has" is incorrect and should be replaced by --have--;

line 41, "would be methodology that does" is incorrect and should be replaced by --methodology: would--;

line 42, "in vitro that is" is incorrect and should be replaced by --*in vitro*; would be--;

line 43, "a" is incorrect and should be removed; and line 45, "and which promotes" is incorrect and should be replaced by--; and would permit--.

UNITED STATES PATENT AND TRADEMARK OFFICE
CERTIFICATE OF CORRECTION

PATENT NO. : 5,077,192
DATED : December 31, 1991
INVENTOR(S) : Liang et al.

It is certified that error appears in the above-indentified patent and that said Letters Patent is hereby corrected as shown below:

Column 4, line 29, "moiety" is incorrect and should be replaced with --moieties--; and line 53, "acid containing" is incorrect and should be replaced by --acid-containing--.

Column 5, line 6, "in vitro" is incorrect and should be replaced with --*in vitro*--;

Column 6, line 67, "in vitro" is incorrect and should be replaced with --*in vitro*--;

Column 8, line 9, "envelop" is incorrect and should be replaced with --envelope--;

Column 8, line 45, "lyzed." should read as follows --lyzed. Nucleic acid liberated from the captured macromolecular entity by heating at high temperature is used as a substrate for amplification and analysis.--;

Column 8, line 62, "Meth. Enzymol." is incorrect and should be replaced with --*Meth. Enzymol.*--;

Column 9, line 11, "the" is incorrect and should be removed; and

Column 9, line 12, "F" is incorrect and should be removed;

lines 57 and 58, "chromotraphy" which bridges these lines is incorrect and should be replaced with --chromotography--.

UNITED STATES PATENT AND TRADEMARK OFFICE
CERTIFICATE OF CORRECTION

PATENT NO. : 5,077,192
DATED : December 31, 1991
INVENTOR(S) : Liang et al.

It is certified that error appears in the above-indentified patent and that said Letters Patent is hereby corrected as shown below:

Column 10, line 37, "*gonorhea*" is incorrect and should be replaced with *gonorrhea*--; and line 66, "character-" is incorrect and should be replaced by --been character- -.

Column 11, line 24, "virons" is incorrect and should be replaced with --virions--.
Column 14, line 45, "patient " is incorrect and should be replaced with --patients-- ; and line 68, "that" is incorrect and should be replaced with --than--.

Column 15, line 11, "that" is incorrect and should be replaced with --than--.
Column 16, line 4 (claim 1, section b.), "sequence" is incorrect and should be replaced with --sequences--.

Signed and Sealed this

Fifteenth Day of February, 1994

BRUCE LEHMAN

Attest:

*Attesting Officer*

*Commissioner of Patents and Trademarks*

UNITED STATES PATENT AND TRADEMARK OFFICE
CERTIFICATE OF CORRECTION

PATENT NO. : 5,077,192

DATED : December 31, 1991

INVENTOR(S) : Liang, et. al.

It is certified that error appears in the above-indentified patent and that said Letters Patent is hereby corrected as shown below:

Column 1, line 25, "source" is incorrect and should be replaced with --sources--;

line 45, "is" is incorrect and should be replaced with --are--; and line 59, "then" is incorrect and should be replaced with --than--.

Column 2, line 3, "was" is incorrect and should be replaced by --is--; and line 22, "a monoclonal antibody" is incorrect and should be replaced with --monoclonal antibodies--;

line 34, "in vitro" is incorrect and should be replaced by --*in vitro*--;

Column 3, line 24, "has" is incorrect and should be replaced by --have--;

line 41, "would be methodology that does" is incorrect and should be replaced by --methodology: would--;

line 42, "in vitro that is" is incorrect and should be replaced by --*in vitro*; would be--;

line 43, "a" is incorrect and should be removed; and line 45, "and which promotes" is incorrect and should be replaced by--; and would permit--.

UNITED STATES PATENT AND TRADEMARK OFFICE
CERTIFICATE OF CORRECTION

PATENT NO. : 5,077,192
DATED : December 31, 1991
INVENTOR(S) : Liang, et. al.

It is certified that error appears in the above-indentified patent and that said Letters Patent is hereby corrected as shown below:

Column 4, line 29, "moiety" is incorrect and should be replaced with --moieties--; and line 53, "acid containing" is incorrect and should be replaced by --acid-containing--.

Column 5, line 6, "in vitro" is incorrect and should be replaced with --*in vitro*--;

Column 6, line 67, "in vitro" is incorrect and should be replaced with --*in vitro*--;

Column 8, line 9, "envelop" is incorrect and should be replaced with --envelope--;

Column 8, line 45, "lyzed." should read as follows --lyzed. Nucleic acid liberated from the captured macromolecular entity by heating at high temperature is used as a substrate for amplification and analysis.--;

Column 8, line 62, "Meth. Enzymol." is incorrect and should be replaced with --*Meth. Enzymol.*--;

Column 9, line 11, "the" is incorrect and should be removed; and

Column 9, line 12, "F" is incorrect and should be removed;

lines 57 and 58, "chromotraphy" which bridges these lines is incorrect and should be replaced with --chromotography--.

UNITED STATES PATENT AND TRADEMARK OFFICE
CERTIFICATE OF CORRECTION

PATENT NO. : 5,077,192
DATED : December 31, 1991
INVENTOR(S) : Liang, et. al.

It is certified that error appears in the above-indentified patent and that said Letters Patent is hereby corrected as shown below:

Column 10, line 37, "*gonorhea*" is incorrect and should be replaced with *gonorrhea--*; and line 66, "character-" is incorrect and should be replaced by --been character- --.

Column 11, line 24, "virons" is incorrect and should be replaced with --virions--.

Column 14, line 45, "patient " is incorrect and should be replaced with --patients-- ; and line 68, "that" is incorrect and should be replaced with --than--.

Column 15, line 11, "that" is incorrect and should be replaced with --than--.

Column 16, line 4 (claim 1, section b.), "sequence" is incorrect and should be replaced with --sequences--.

UNITED STATES PATENT AND TRADEMARK OFFICE
CERTIFICATE OF CORRECTION

PATENT NO. : 5,077,192
DATED : December 31, 1991
INVENTOR(S) : Liang, et. al.

It is certified that error appears in the above-indentified patent and that said Letters Patent is hereby corrected as shown below:

Column 12, line 7, "1906" should read —1917—; line 47, "(bold" should read — (sequences in bold—; and the formulas in the left hand column should appear as follows:

Hind III
5'-TGAAGCTCACCATATTCTTGGGAACAAGA-3'
   /                              /
  3151                           3132

Bam HI
5'-ATGGATCCTCCTGCCTCCACCAATCG-3'
   /                         /
  3111                      3130

Sac I
5'-CCGAGCTCGTGTTACAGGCGGGGTTTTTCTTGT-3'
   /                                /
  193                              220

Bam HI
5'-ATGGATCCTGGTTATCGCTGGATGTGTCTGCGG-3'
   /                                /
  363                              390

UNITED STATES PATENT AND TRADEMARK OFFICE
CERTIFICATE OF CORRECTION

PATENT NO. : 5,077,192
DATED : December 31, 1991
INVENTOR(S) : Liang, et. al.

It is certified that error appears in the above-indentified patent and that said Letters Patent is hereby corrected as shown below:

the formulas in the right hand portion of column 12 should appear as follows:

```
              Xho I
5'CTCTCGAGTAGGCTGCCTTCCTGACTG-3'
    /                      /
  2825                   2847

Sac I
5'-CTGAGCTCTGCGGTATTGTGAGGATTCTTGTCA-3'
    /                            /
   248                          221

Xho I
5'-AACTCGAGGCATAGCAGCAGGATGAAGAGGAA-3'
    /                           /
   429                         403

Bgl II
5'-AAAGATCTGAGGCCCACTCCCATAGG-3'
    /                      /
   658                    639
```

Column 13, top of page, the formulas should appear as follows:

```
              Xba I
5'-CGTCTAGAAATTGCACCTGTATTCCCATCCCATC-3'
    /                              /
   589                            617
```

UNITED STATES PATENT AND TRADEMARK OFFICE
CERTIFICATE OF CORRECTION

PATENT NO. : 5,077,192
DATED : December 31, 1991
INVENTOR(S) : Liang, et. al.

It is certified that error appears in the above-indentified patent and that said Letters Patent is hereby corrected as shown below:

Column 13, line 33, "performed" is incorrect and should be replaced with --were performed--; and line 53, "correspond" is incorrect and should be replaced with --corresponds--.

Column 14, top of page, the formula should appear as follows:

```
          Hind III
5'-GT AAGCTT AGGGTTTAAATGTATACCCA-3'
       /                        /
      844                      823
```

Column 14, line 45, "patient" is incorrect and should be replaced with --patients-- ; and line 68, "that" is incorrect and should be replaced with --than--.

UNITED STATES PATENT AND TRADEMARK OFFICE
CERTIFICATE OF CORRECTION

PATENT NO. : 5,077,192
DATED : December 31, 1991
INVENTOR(S) : Liang, et. al.

It is certified that error appears in the above-indentified patent and that said Letters Patent is hereby corrected as shown below:

Column 15, line 11, "that" is incorrect and should be replaced with --than--

This certificate supersedes Certificate of Correction issued February 15, 1994.

Signed and Sealed this

Twenty-fourth Day of January, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,077,192

DATED : December 31, 1991

INVENTOR(S) : Liang et al.

It is certified that error appears in the above-indentified patent and that said Letters Patent is hereby corrected as shown below:

Column 1, line 25, "source" is incorrect and should be replaced with --sources--;
  line 45, "is" is incorrect and should be replaced with --are--; and
  line 59, "then" is incorrect and should be replaced with --than--.

Column 2, line 3, "was" is incorrect and should be replaced with --is--;
  line 22, "a monoclonal antibody" is incorrect and should be replaced with --monoclonal antibodies--; and
  line 34, "in vitro" is incorrect and should be replaced with --*in vitro*--.

Column 3, line 24, "has" is incorrect and should be replaced with --have--;
  line 41, "would be methodology that does" is incorrect and should be replaced with --methodology: would--;
  line 42, "in vitro that is" is incorrect and should be replaced with --*in vitro*; would be--;
  line 43, "a" is incorrect and should be removed; and
  line 45, "and which promotes" is incorrect and should be replaced with --; and would permit--.

Column 4, line 29, "moiety" is incorrect and should be replaced with --moieties--; and
  line 53, "acid containing" is incorrect and should be replaced with --acid-containing--.

Column 5, line 6, "in vitro" is incorrect and should be replaced with --*in vitro*--.

Column 6, line 67, "in vitro" is incorrect and should be replaced with --*in vitro*--.

UNITED STATES PATENT AND TRADEMARK OFFICE
CERTIFICATE OF CORRECTION

PATENT NO. : 5,077,192

DATED : December 31, 1991

INVENTOR(S): Liang et al.

It is certified that error appears in the above-identified patent and that said Letters Patent is hereby corrected as shown below.

Column 8, line 9, "envelop" is incorrect and should be replaced with --envelope--;

line 45, "lyzed." should read as follows --lyzed. Nucleic acid liberated from the captured macromolecular entity by heating at high temperature is used as a substrate for amplification and analysis.--; and line 62, "Meth. Enzymol." is incorrect and should be replaced with --*Meth. Enzymol.*--.

Column 9, line 11, "the" is incorrect and should be removed;

line 12, "F" is incorrect and should be removed; and lines 57 and 58, "chromotraphy" which bridges these lines is incorrect and should be replaced with --chromotography--.

Column 10, line 37, "*gonorhea*" is incorrect and should be replaced with --*gonorrhea*--; and line 66, "character-" is incorrect and should be replaced with --been character- --.

Column 11, line 5, "the a domain" is incorrect and should be replaced with --the a domain--; and line 24, "virons" is incorrect and should be replaced with --virions--.

Column 12, line 7, "1906" is incorrect and should be replaced with --1917--; and line 47, "(bold" is incorrect and should be replaced with --(sequences in bold--.

UNITED STATES PATENT AND TRADEMARK OFFICE
CERTIFICATE OF CORRECTION

PATENT NO. : 5,077,192
DATED : December 31, 1991
INVENTOR(S) : Liang et al.

It is certified that error appears in the above-indentified patent and that said Letters Patent is hereby corrected as shown below:

Column 12, the formulas in the left hand column should appear as follows:

```
       Hind III
5'-TGAAGCTCACCATATTCTTGGGAACAAGA-3'
     /                         /
   3151                      3132

Bam HI
5'-ATGGATCCTCCTGCCTCCACCAATCG-3'
     /                       /
   3111                    3130

Sac I
5'-CCGAGCTCGTGTTACAGGCGGGGTTTTTCTTGT-3'
     /                              /
   193                             220

Bam HI
5'-ATGGATCCTGGTTATCGCTGGATGTGTCTGCGG-3'
     /                              /
   363                             390
```

UNITED STATES PATENT AND TRADEMARK OFFICE
CERTIFICATE OF CORRECTION

PATENT NO. : 5,077,192

DATED : December 31, 1991

INVENTOR(S) : Liang et al.

It is certified that error appears in the above-indentified patent and that said Letters Patent is hereby corrected as shown below:

Column 12, the formulas in the right hand column should appear as follows:

```
          Xho I
5'-CTCTCGAGTAGGCTGCCTTCCTGACTG-3'
     /                    /
    2825                 2847

Sac I
5'-CTGAGCTCTGCGGTATTGTGAGGATTCTTGTCA-3'
       /                          /
      248                        221

Xho I
5'-AACTCGAGGCATAGCAGCAGGATGAAGAGGAA-3'
     /                            /
    429                          403

Bgl II
5'-AAAGATCTGAGGCCCACTCCCATAGG-3'
     /                      /
    658                    639
```

UNITED STATES PATENT AND TRADEMARK OFFICE
CERTIFICATE OF CORRECTION

PATENT NO. : 5,077,192

DATED : December 31, 1991

INVENTOR(S) : Liang et al.

It is certified that error appears in the above-indentified patent and that said Letters Patent is hereby corrected as shown below:

Column 13, top of page, the formula should appear as follows:

```
                    Xba I
    5'-CGTCTAGAAATTGCACCTGTATTCCCATCCCATC-3'
       /                                 /
      589                               617
``` and

Column 13, line 33, "performed" is incorrect and should be replaced with --were performed--;

line 53, "correspond" is incorrect and should be replaced with --corresponds--.

Column 14, top of page, the formula should appear as follows:

```
         Hind III
    5'-GTAAGCTTAGGGTTTAAATGTATACCCA-3'
       /                          /
      844                        823
```

UNITED STATES PATENT AND TRADEMARK OFFICE
CERTIFICATE OF CORRECTION

PATENT NO. : 5,077,192

DATED : December 31, 1991

INVENTOR(S) : Liang et al.

It is certified that error appears in the above-indentified patent and that said Letters Patent is hereby corrected as shown below:

Column 14, line 23, "(" is incorrect and should be removed;
  line 45, "patient" is incorrect and should be replaced with --patients--; and
  line 68, "that" is incorrect and should be replaced with --than--.

Column 15, line 11, "that" is incorrect and should be replaced with --than--; and
  line 18, "TGI" is incorrect and should be replaced with --TG1--.

Column 16, line 4 (claim 1, section b.), "sequence" is incorrect and should be replaced with --sequences--.

This certificate supersedes Certificate of Correction issued January 24, 1995.

Signed and Sealed this

Second Day of September, 1997

Attest:

BRUCE LEHMAN

*Attesting Officer*  *Commissioner of Patents and Trademarks*